United States Patent
Zhang et al.

(10) Patent No.: US 9,656,250 B2
(45) Date of Patent: May 23, 2017

(54) METHOD FOR PREPARING IODINE-DOPED $TIO_2$ NANO-CATALYST AND USE THEREOF IN HETEROGENEOUSLY CATALYZING CONFIGURATION TRANSFORMATION OF TRANS-CAROTENOIDS

(71) Applicant: Jiangnan University, Wuxi (CN)

(72) Inventors: Lianfu Zhang, Wuxi (CN); Qingrui Sun, Wuxi (CN); Hongxiao Yan, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 166 days.

(21) Appl. No.: 14/617,945

(22) Filed: Feb. 10, 2015

(65) Prior Publication Data

US 2016/0158736 A1   Jun. 9, 2016

(30) Foreign Application Priority Data

Dec. 5, 2014   (CN) .......................... 2014 1 0736320

(51) Int. Cl.
| | | |
|---|---|---|
| *B01J 27/135* | (2006.01) | |
| *C07C 403/24* | (2006.01) | |
| *C07C 403/00* | (2006.01) | |
| *C07C 5/22* | (2006.01) | |

(52) U.S. Cl.
CPC ........... *B01J 27/135* (2013.01); *C07C 5/2213* (2013.01); *C07C 403/00* (2013.01); *C07C 403/24* (2013.01); *C07C 2101/16* (2013.01); *C07C 2527/135* (2013.01)

(58) Field of Classification Search
None
See application file for complete search history.

(56) References Cited

U.S. PATENT DOCUMENTS

| | | | |
|---|---|---|---|
| 7,126,036 B2 | 10/2006 | Wegner et al. | |
| 2003/0220525 A1* | 11/2003 | Khachik | ............... C07C 403/24 568/365 |
| 2010/0167914 A1* | 7/2010 | Anderson | .............. B01J 21/063 502/80 |
| 2013/0337418 A1* | 12/2013 | Anuradha | ................ A01N 3/00 434/93 |
| 2014/0023712 A1* | 1/2014 | Helgason | ............... A23L 1/2753 424/489 |
| 2015/0233010 A1* | 8/2015 | Pan | ........................ C25D 11/34 205/322 |
| 2015/0272835 A1* | 10/2015 | Mitsuhashi | ............. C12P 23/00 424/401 |

FOREIGN PATENT DOCUMENTS

| | | |
|---|---|---|
| CN | 101314554 | 12/2008 |
| CN | 101575256 | 11/2009 |
| WO | WO 02/072509 | 9/2002 |
| WO | WO 2008/017401 | 2/2008 |

* cited by examiner

*Primary Examiner* — Tam M Nguyen
(74) *Attorney, Agent, or Firm* — Gokalp Bayramoglu

(57) ABSTRACT

The present invention relates to a method for preparing an iodine-doped $TiO_2$ nano-catalyst and use of the catalyst in heterogeneously catalyzing configuration transformation of trans-carotenoids. The iodine-doped $TiO_2$ nano-catalyst is prepared by a sol-gel process using a titanate ester as a precursor and an iodine-containing compound as a dopant in the presence of a diluent, inhibitor and complexing agent. The catalyst exhibits high activity for isomerization of the trans-carotenoids into their cis-isomers within a short catalytic time. The catalyst can be easily prepared and is highly efficient, economical, recyclable and environmentally friendly.

3 Claims, 4 Drawing Sheets

METHOD FOR PREPARING IODINE-DOPED TIO₂ NANO-CATALYST AND USE THEREOF IN HETEROGENEOUSLY CATALYZING CONFIGURATION TRANSFORMATION OF TRANS-CAROTENOIDS

BACKGROUND OF THE INVENTION

Field of the Invention

The present invention relates to a nano-catalyst and preparation method thereof, and in particular, to a highly active iodine-doped $TiO_2$ nano-catalyst and preparation method thereof, as well as use thereof in transformation of trans-carotenoids into their cis-isomers, which belongs to the field of production of inorganic nano catalytic materials and health food.

Description of Related Art

Carotenoids are a class of compounds having special physiological functions and pharmacological functions and are important on human health. Because of the effects of steric hindrance by methylation, the conjugated double bond in the molecule cannot rotate freely, carotenoids may have many stereoisomers. But, in fact, carotenoids normally have much less stereoisomers than theoretical number. For example, common cis-lycopenes include 5-cis-, 7-cis-, 9-cis-, 13-cis- and 15-cis-isomers, and cis-β-carotenes include 9-cis-, 13-cis- and 15-cis-isomers.

Natural carotenoids in food (for example, tomato) are dominantly in all-trans-structure, but mainly in cis-configuration in human tissues and cells. Existing study results suggest that carotenoids in cis-configuration, such as cis-lycopenes and cis-β-carotenes, usually have higher biological potency and stronger physiological activity than their all-trans-isomers. In addition, among cis-lycopenes, 5-cis-isomer presents maximal antioxidant activity and stability, and among cis-β-carotenes, 9-cis-isomer has the maximal activity in inhibiting atherosclerosis and reducing incidence of cancers. Therefore, increasing the proportion of cis-configuration in carotenoids, in particular increasing the proportion of 5-cis-lycopene in lycopenes or 9-cis-β-carotene in β-carotenes, is expected to greatly improve physiological activity of carotenoid products.

Common methods for increasing the proportion of cis-configuration carotenoids using natural carotenoids as raw material include thermal isomerization and photoisomerization.

The thermal isomerization is to promote transformation of all-trans configuration into cis configuration by heating at reflux in an organic phase or by directly heating under special conditions. Patents PCT/EP2007/006747, PCT/EP02/00708, U.S. Pat. No. 7,126,036 and CN101575256 have disclosed a method for preparing cis-lycopenes by heating at reflux in an organic phase, respectively, but these methods have the disadvantages of complicated operation, long processing time and low in 5-cis-lycopene content.

The photoisomerization can be divided into direct photoisomerization and iodine-catalyzed photoisomerization. In direct photoisomerization, groups at a double bond in an active ingredient are subjected to trans-cis configuration transformation in the environment without oxygen, at certain temperature, under light of certain wavelength range. CN101314554 has disclosed a method for preparing cis-lycopene isomers with all-trans-lycopene as raw materials using direct photoisomerization. The photoisomerization has significant drawbacks, such as requiring special reaction apparatus, difficult in expanding reaction scale; As for $I_2$ catalyzed configuration, its disadvantages include the loss of $I_2$ by sublimation and the removal difficulty of $I_2$ after the reaction, so the safety of the product cannot be ensured, and the production cost is inevitably increased.

Nano $TiO_2$ has high chemical and thermal stability, no toxicity and non-mobility and is allowed to contact with food, and therefore has been widely used in the industry of food packing materials. Thus, use of nano $TiO_2$ as support of active iodine is further helpful to meet people's demands on food safety.

SUMMARY OF THE INVENTION

Technical Problem

The object of the present invention is to overcome the shortcomings in prior art, which is achieved by providing a method for preparing an iodine-doped $TiO_2$ nano-catalyst. The catalyst can be used for catalyzing natural lycopene or β-carotene to prepare the products with a high cis-configuration proportion, the latter can be used as common food ingredient, functional food material or diet supplement material.

Technical Solution

The technical solution of the present invention is as follows:

A method for preparing an iodine-doped $TiO_2$ nano-catalyst, comprising the steps of:

(1) adding an iodine-containing compound and a complexing agent into an aqueous solution of 80%-95% ethanol and uniformly mixing to give a mixture A:

(2) adding a titanate ester into a diluent and then adding an inhibitor, and uniformly mixing to give a mixture B;

(3) slowly adding dropwise the mixture B into the mixture A at RT with vigorous stirring, and further stirring for 2-6 h after the addition is completed;

(4) placing the reaction solution from the step (3) into a wide-mouthed container to stand for aging for 1-6 days, to give a $TiO_2$ gel:

(5) drying the $TiO_2$ gel from the step (4) at 60-100° C. under a vacuum degree of 0.1 MPa for 12 h, and then initially grinding into $TiO_2$ powder; and (6) baking the $TiO_2$ powder from the step (5) at 160-220° C. under a vacuum degree of 0.1 MPa for 2.0-4.0 h, and then re-grinding into an iodine-doped $TiO_2$ nano-catalyst.

The iodine-containing compound is potassium iodide or sodium iodide;

The titanate ester is tetrabutyl titanate or tetraisopropyl titanate;

The diluent is absolute ethanol;

The inhibitor is acetic acid or acetyl acetone; and

The complexing agent is polyvinyl pyrrolidone or polyethylene glycol.

The ratio by weight of the iodine-containing compound and the titanate ester is 2:100-6:100;

The ratio by volume of the diluent and the titanate ester is 1:2-10:1;

The ratio by volume of the inhibitor and the titanate ester is 1:20-1:2; and

The ratio by weight of the complexing agent and the iodine-containing compound is 1:50-1:20.

Use of the iodine-doped $TiO_2$ nano-catalyst in heterogeneously catalyzed configuration transformation of trans-carotenoids is in that trans-lycopenes or β-carotenes, the catalyst and ethyl acetate are heated away from light at reflux, and after the reaction is completed, the reaction solution is cooled, centrifuged to isolate the catalyst, and then evaporated under vacuum to remove ethyl acetate to give lycopenes or β-carotenes having a high cis-configuration proportion.

Advantageous Effects

In the prior art, elemental iodine, $I_2$, is simply used as catalyst in photo configuration transformation of trans-carotenoids. In order to reduce iodine content in the product, the reaction solution has to be washed many times with an aqueous solution of sodium thiosulfate, then with purified water, which leads to not only low production efficiency, but also pollution on environment and waste in iodine resource.

In the present invention, a wet $TiO_2$ gel is firstly prepared using a sol-gel process with a titanate ester as precursor and an iodine-containing compound as dopant, in the presence of a diluent, inhibitor and complexing agent, and then the gel is aged, vacuum dried, initially ground, vacuum baked, and re-ground to give a highly active iodine-doped $TiO_2$ nano-catalyst. The resulting catalyst can heterogeneously catalyze configuration transformation of trans-carotenoids in an organic phase in the absence of light, so that difficulty in separating the iodine-containing compound and the catalyst, non-recyclability, excess iodine residual in the product which are present in homogeneous catalysis are solved, which also represents an innovative aspect of the invention.

The catalyst obtained in the present application displays high activity for catalyzing isomerisation of trans-carotenoids into their cis-isomers. For isomerisation of lycopenes, total cis-lycopene proportion in the product reaches more than 75%, and for isomerisation of β-carotenes, total cis-β-carotene proportion in the product reaches more than 50%, and also a high content of 5-cis-lycopene and 9-cis-β-carotene can be obtained, but the processing time is only ⅕ of that of exiting thermal reflux isomerisation and ½ of that of photocatalytic isomerisation. The catalyst has a simple preparation process and is highly efficient, economical, recyclable and environmentally friendly. The cis-carotenoids obtained by the catalyst facilitate improvement of functionalities of health food, thereby expanding the application field of carotenoids.

DETAILED DESCRIPTION OF THE INVENTION

Figure 1:
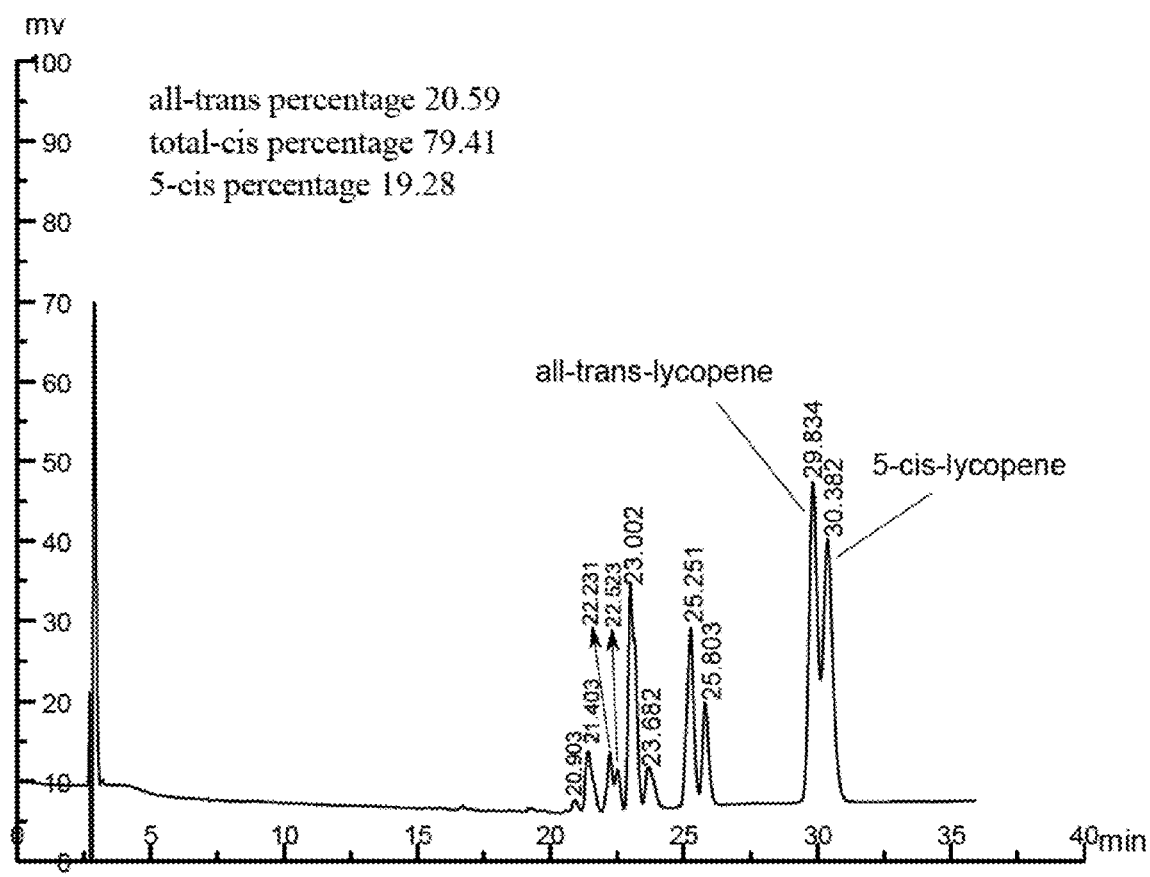
FIG. 1 is a HPLC spectrum in which the catalyst obtained in example 5 is used for catalytic isomerisation of all-trans-lycopene (purity: 90%) for 2 h following the catalyst activity evaluation in the summary of the invention. It can be known from FIG. 1 that the relative percentage of total cis-lycopenes is 79.41, of which the relative percentage of 5-cis-lycopene is 19.28.
Figure 2:
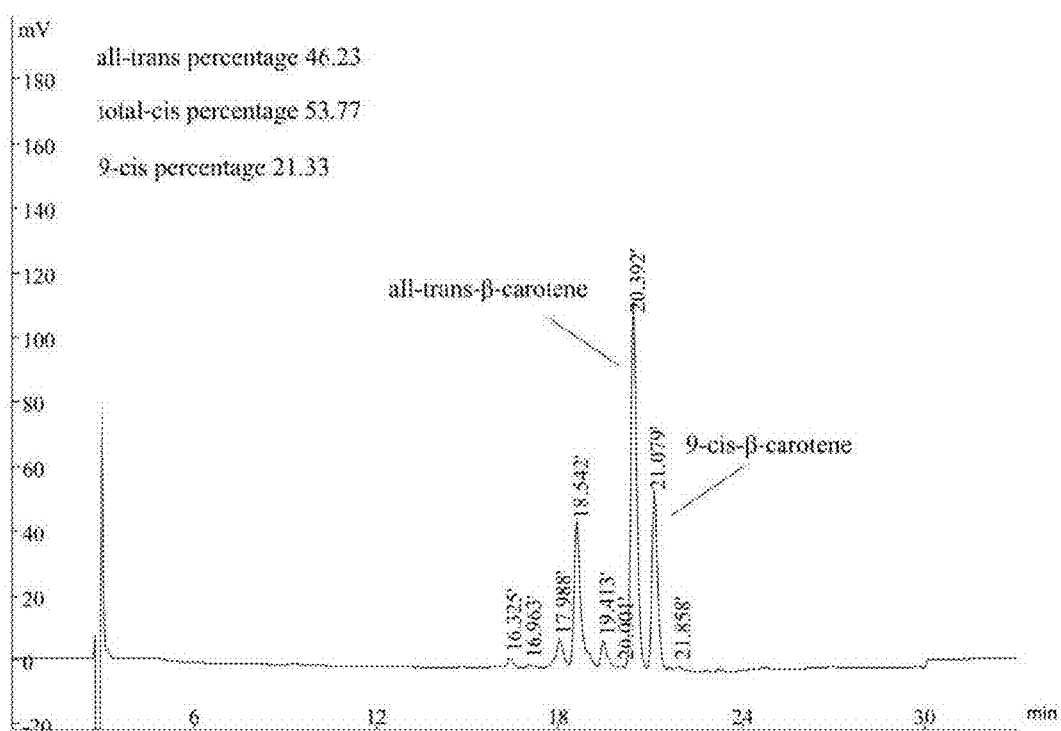
FIG. 2 is a HPLC spectrum in which the catalyst obtained in example 5 is used for catalytic isomerisation of all-trans-β-carotene (purity: 90%) for 2 h following the catalyst activity evaluation in the summary of the invention. It can be known from FIG. 2 that the relative percentage of total cis-β-carotenes is 53.77, of which the relative percentage of 9-cis-β-carotene is 21.33.
Figure 3:
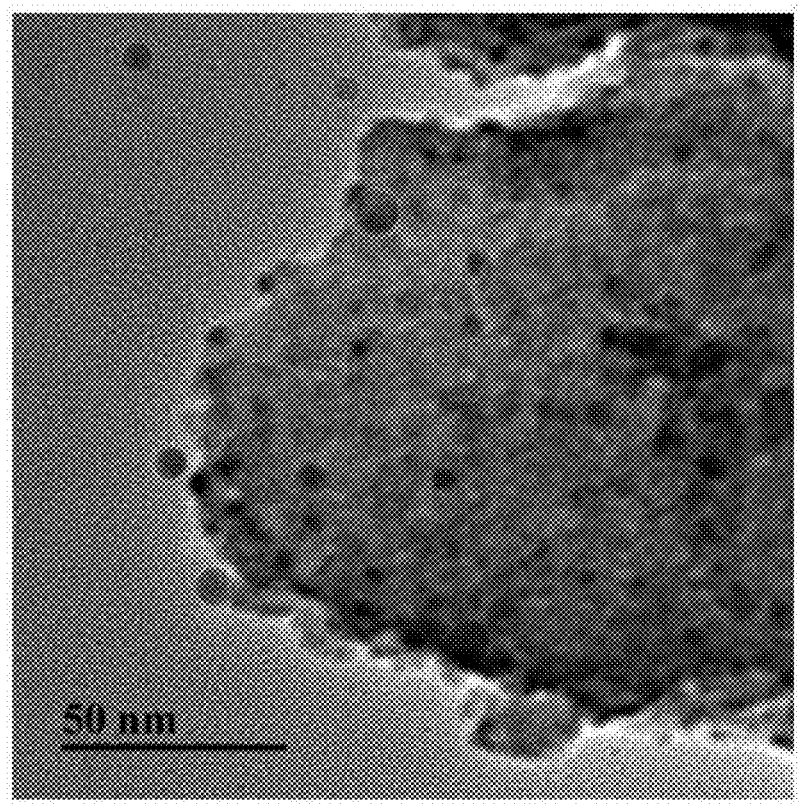
FIG. 3 is a TEM image of the catalyst obtained in example 5. It can be seen from FIG. 3 that the catalyst is nano-sized particles.
Figure 4:
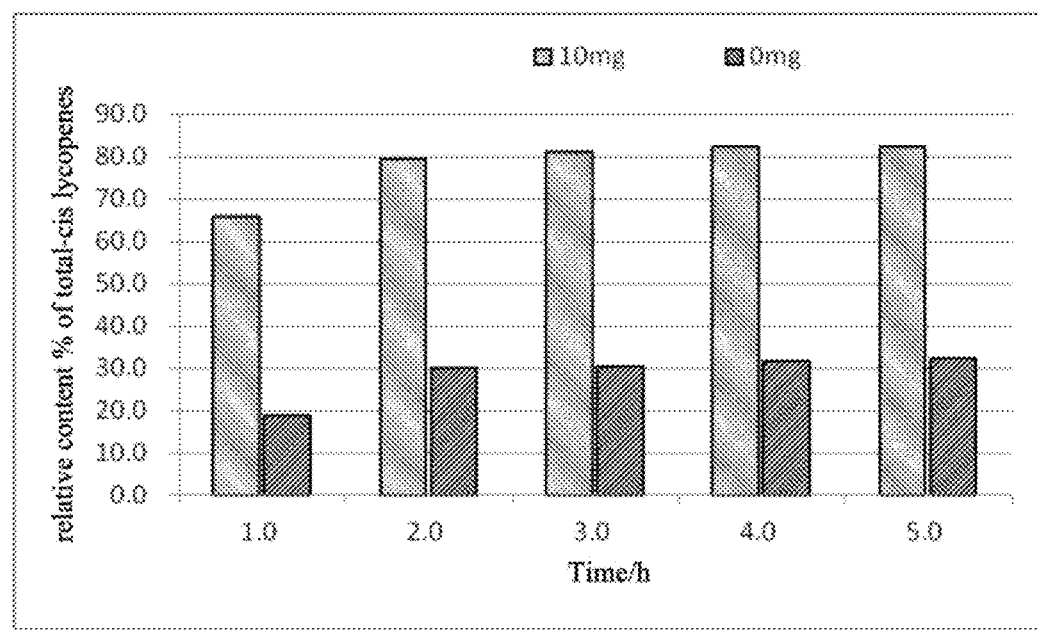
FIG. 4 is a histogram showing comparison of results of lycopene isomerisation with time in the presence of the catalyst (10 mg) obtained in example 5 and in the absence of the catalyst. It can be seen from FIG. 3 that for catalytic reaction for 1 h to 2 h, the relative percentage of total cis-lycopenes increases from 65.81 to 79.41, and for non-catalyzed thermal isomerisation, the relative percentage only increases from 18.64 to 29.84; for catalytic reaction up to 5 h, the relative percentage of total cis-lycopenes is 82.36, and for non-catalyzed reaction, the relative percentage only is 32.19. This indicates that the catalyst obtained in the present application is capable of greatly improving the isomerisation rate of lycopenes.

For a better understanding of the present invention, the present invention is further described below in connection with specific embodiments, but the scope of the present invention is not limited to thereto.

All the reagents used in the examples of the present invention are purchased from Sinopharm Chemical Reagent Co., Ltd (China), and unless otherwise specified, are analytically pure, in which tetrabutyl titanate (relative density: 0.996) and tetraisopropyl titanate are chemically pure.

Example 1

(1) 200 mg KI and 4 mg polyvinyl pyrrolidone were added into a 60 mL aqueous solution of 80% ethanol at normal temperature, and uniformly mixed to give a mixture A;

(2) 10 mL tetrabutyl titanate (about 10 g) was added into 5 mL absolute ethanol, and then 0.5 mL acetic acid was added and uniformly mixed to give a mixture B;

(3) the mixture B was slowly added dropwise into the mixture A at RT with vigorous stirring, and further stirred for 2 h after the addition is completed;

(4) the reaction solution from the step (3) was placed into a wide-mouthed container to stand for aging for 1 day, to give a $TiO_2$ gel;

(5) the $TiO_2$ gel from the step (4) was dried at 60° C. under a vacuum degree of 0.1 MPa for 12 h, and then initially ground into $TiO_2$ powder; and (6) the $TiO_2$ powder from the step (5) was calcined at 160° C. under a vacuum degree of 0.1 MPa for 2.0 h, and then re-ground into an iodine-doped $TiO_2$ nano-catalyst.

Evaluation of Catalytic Activity:

To a 25 mL round-bottomed flask were added 20 mug lycopenes or β-carotenes at a purity of 90%, 10 mg the catalyst and 20 mL ethyl acetate. The flask was attached with a condensing means and a nitrogen purging of oxygen means, placed in a water bath at 77° C. to react away from light for 2 h, and cooled in an ice-water bath. 100 μL of the reaction solution was taken, made up to with ethyl acetate to 5 mL, and filtered through a 0.22 μm filter membrane. Then, the relative percentage of each isomer was detected with a liquid chromatograph using an area normalization method at 472 nm for lycopenes and at 450 nm for β-carotenes. Chromatographic column: YMC C30 column (5 μm, 250 mm×4.6 mm); mobile phase:A phase:methanol:acetonitrile=25:75, B phase: methyl t-butyl ether 100%; gradient conditions: 0-20 min, A phase from 100% to 50%, 20-40 min, A phase constant at 50%; sample solvent: ethyl acetate; flow rate: 1 mL/min; column temperature: 30° C.; and injection volume: 20 μL. The relative percentage of total cis-lycopenes is 59.21, and the relative percentage of total cis-β-carotenes is 34.37.

Materials and Process Conditions Employed in the Steps of Examples 2 to 6 are Shown in Table 1 Below:

TABLE 1

| step | process and materials | example 2 | example 3 | example 4 | example 5 | example 6 |
|---|---|---|---|---|---|---|
| (1) | iodine-containing compound | KI 600 mg | KI 300 mg | KI 350 mg | KI 450 mg | NaI 400 mg |
|  | complexing agent | polyvinyl pyrrolidone 30 mg | polyvinyl pyrrolidone 10 mg | polyvinyl pyrrolidone 10 mg | polyvinyl pyrrolidone 15 mg | polyethylene glycol 20 mg |
|  | aqueous ethanol solution | 60 mL 95% ethanol | 60 mL 90% ethanol | 60 mL 95% ethanol | 60 mL 90% ethanol | 60 mL 80% ethanol |
| (2) | titanate ester | tetrabutyl titanate 10 mL | tetrabutyl titanate 10 mL | tetrabutyl titanate 10 mL | tetrabutyl titanate 10 mL | tetraisopropyl titanate 10 mL |
|  | diluent | ethanol 100 mL | ethanol 20 mL | 10 mL ethanol | 10 mL ethanol | 10 mL ethanol |
|  | inhibitor | acetic acid 5 mL | acetic acid 2 mL | acetic acid 2 mL | acetic acid 3 mL | acetyl acetone 2 mL |
| (3) | mixing and then stirring | 6 h | 5 h | 3 h | 3 h | 4 h |
| (4) | aging | 6 days | 3 days | 5 days | 4 days | 4 days |
| (5) | vacuum drying | 0.1 MPa\100° C.\12 h | 0.1 MPa\80° C.\12 h | 0.1 MPa\85° C.\12 h | 0.1 MPa\80° C.\12 h | 0.1 MPa\80° C.\12 h |
| (6) | Vacuum calcining | 0.1 MPa\220° C.\4.0 h | 0.1 MPa\180° C.\3 h | 0.1 MPa\185° C.\2 h | 0.1 MPa\195° C.\2 h | 0.1 MPa\185° C.\2 h |
| Evaluation of catalytic activity/relative percentage | total cis-lycopenes | 43.51 | 68.51 | 76.27 | 79.41 | 78.65 |
|  | total cis-β-carotenes | 29.69 | 44.38 | 49.97 | 53.77 | 51.06 |

Comparing Comparative Example 1 and Comparative Example 2 with Example 5, Materials and Process Conditions Employed in the Steps are Shown in Table 2 Below:

TABLE 2

| step | process and materials | comparative example 1 | comparative example 2 |
|---|---|---|---|
| (1) | iodine-containing compound | KI 450 mg | KI 450 mg |
|  | complexing agent | 0 mg | polyvinyl pyrrolidone 15 mg |
|  | aqueous ethanol solution | 60 mL 90% ethanol | 60 mL 90% ethanol |
| (2) | titanate ester | tetrabutyl titanate 10 mL | tetrabutyl titanate 10 mL |
|  | diluent | ethanol 10 mL | 10 mL ethanol |
|  | inhibitor | acetic acid 3 mL | acetic acid 3 mL |
| (3) | mixing and then stirring | 3 h | 3 h |
| (4) | aging | 4 days | 4 days |
| (5) | drying | vacuum degree 0.1 MPa\80° C.\12 h | atmospheric air\80° C.\12 h |
| (6) | calcining | vacuum degree 0.1 MPa\195° C.\2 h | atmospheric air\195° C.\2 h |
| Evaluation of catalytic activity/relative percentage | total cis-lycopenes | 42.26 | 37.53 |
|  | total cis-β-carotenes | 26.72 | 23.16 |

It can be known by comparing catalysis results between comparative example 1 in table 2 and example 5 that, the complexing agent, polyvinyl pyrrolidone, facilitates improvement of the activity of the catalyst, possibly due to the fastening effect of polyvinyl pyrrolidone on active iodine in nano $TiO_2$ meso-pore at a certain temperature; and it can be known by comparing catalysis results between comparative example 2 and example 5 that, the vacuum drying-vacuum calcining process facilitates improvement of the activity of the catalyst, possibly due to difficulty in oxidation of active iodine in nano $TiO_2$ meso-pore into inactive iodate with high-valent iodine, so that the catalyst has a higher activity than that in the atmospheric air drying-atmospheric air calcining process.

The invention is not in any way limited to the embodiments described above, and all equivalent modifications and variations of this invention fall within the scope of the present invention.

What is claimed is:

1. The method of using an iodine-doped $TiO_2$ nano-catalyst in heterogeneously catalyzing configuration transformation of trans-carotenoids into their cis-isomers, the method comprising:
    dissolving trans-lycopenes or β-carotenes in ethyl acetate;
    adding a predetermined amount of said iodine-doped $TiO_2$ nano-catalyst;
    heating to refluxing in darkness for a fixed period of time to form a mixture;
    cooling the mixture to a room temperature;
    centrifuging the mixture to isolate the catalyst; and
    evaporating the solution under vacuum to remove ethyl acetate to form a reside product lycopene or β-carotene with a high proportion of cis-configuration.

2. The method of using the iodine-doped nano-catalyst in heterogeneously catalyzing configuration transformation of trans-carotenoids according to claim 1, wherein, the method is used for catalytic isomerization of lycopene to form the reside product having 19.28% 5-cis-lycopene.

3. The method of using the iodine-doped TiO$_2$ nanocatalyst in heterogeneously catalyzing configuration transformation of trans-carotenoids according to claim 1, wherein, the method is used for catalytic isomerization of β-carotene to form the reside product having 21.33% 9-cis-β-carotene.

* * * * *